United States Patent [19]

Hamilton

[11] Patent Number: 5,207,674
[45] Date of Patent: May 4, 1993

[54] ELECTRONIC CRYOGENIC SURGICAL PROBE APPARATUS AND METHOD

[76] Inventor: Archie C. Hamilton, 3422 Rolling Hills Dr., Eagan, Minn. 55121

[21] Appl. No.: 699,994

[22] Filed: May 13, 1991

[51] Int. Cl.⁵ .............................................. A61B 17/36
[52] U.S. Cl. ...................................... 606/20; 606/21; 606/23
[58] Field of Search ..................... 606/20–26

[56] References Cited

U.S. PATENT DOCUMENTS

| | | | |
|---|---|---|---|
| 3,093,135 | 6/1963 | Hirschhorn | 606/20 |
| 3,327,713 | 6/1967 | Eidus | 606/20 X |
| 3,369,549 | 2/1968 | Armao | 606/21 |
| 3,929,136 | 12/1975 | Kreeb et al. | 606/25 |
| 3,948,269 | 4/1976 | Zimmer | 606/24 |
| 4,200,104 | 4/1980 | Harris | 606/23 X |
| 4,860,744 | 8/1989 | Johnson et al. | 606/21 X |

FOREIGN PATENT DOCUMENTS 239048 9/1987 European Pat. Off. ............. 606/20

OTHER PUBLICATIONS

Soviet Patents Abstracts, Section PQ, 25 Aug. 1982, Derwent Publications, Ltd., London, GB; Class P31, AN 82-J4247E & SU,A,865 286 (Ivchenko).

Wilcox and Giesler, Jr., "An Instrument Using a Multiple Layer Peltier Device to Change Skin Temperature Rapidly," *Brain Research Bulletin*, vol. 12, pp. 143–146, 1984.

*Primary Examiner*—Peter A. Aschenbrenner
*Attorney, Agent, or Firm*—Merchant, Gould, Smith, Edell, Welter & Schmidt

[57] ABSTRACT

A thermoelectric cryoprobe for the topical treatment of neoplasms by freezing. The cryoprobe comprises a plurality of stacked thermoelectric modules coupled to a distal treatment tip through a heat pipe. Heat is dissipated by a heat exchanger system. An external control unit is provided which serves as a source of DC power for the hand-held cryoprobe and contains a control system for controlling the thermoelectric element based upon temperature feedback from treatment site. Temperature feedback from the sensors facilitates freeze-thaw cycling by the cryoprobe to more effectively destroy the tissue at the treatment site.

31 Claims, 6 Drawing Sheets

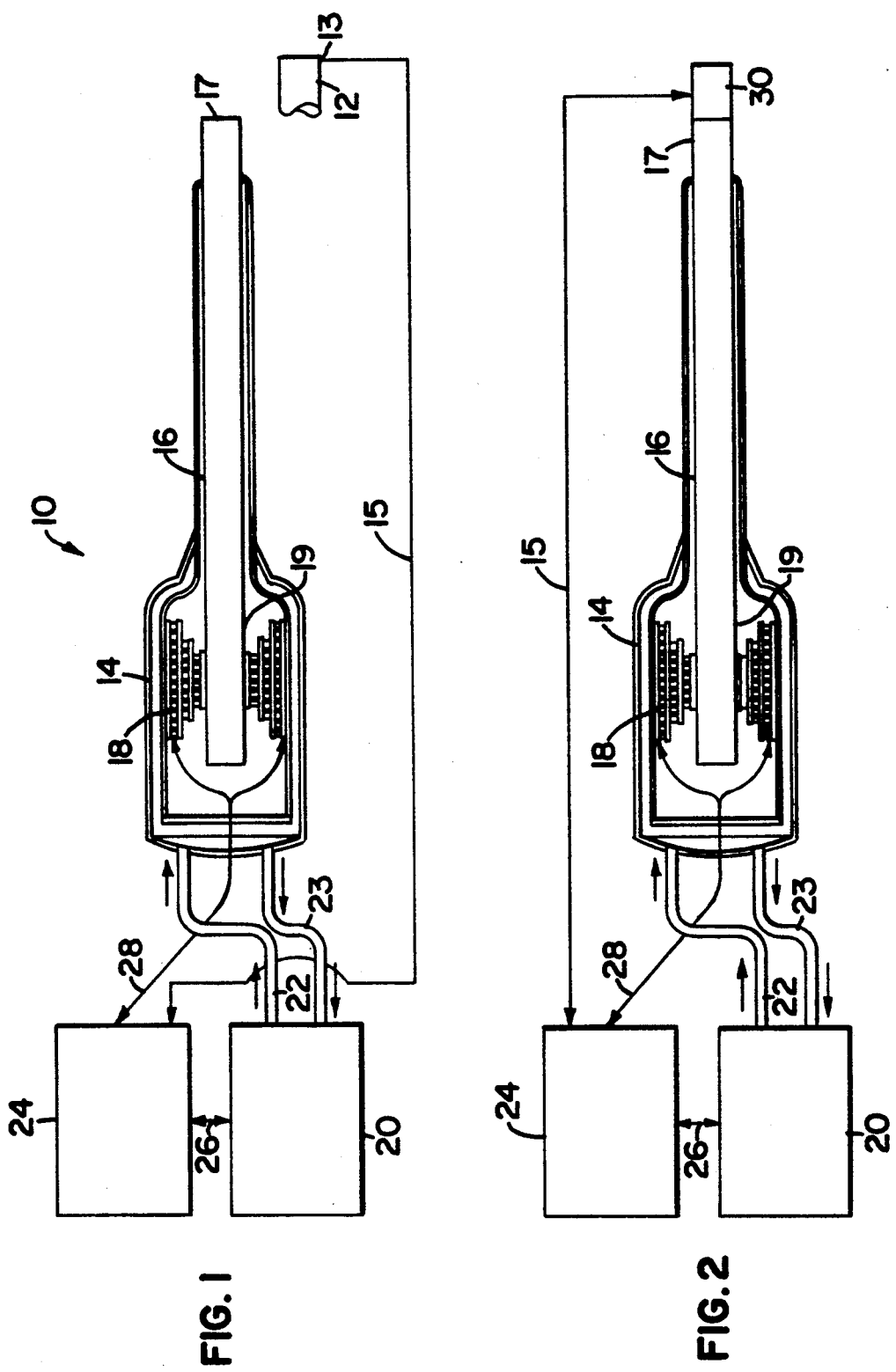

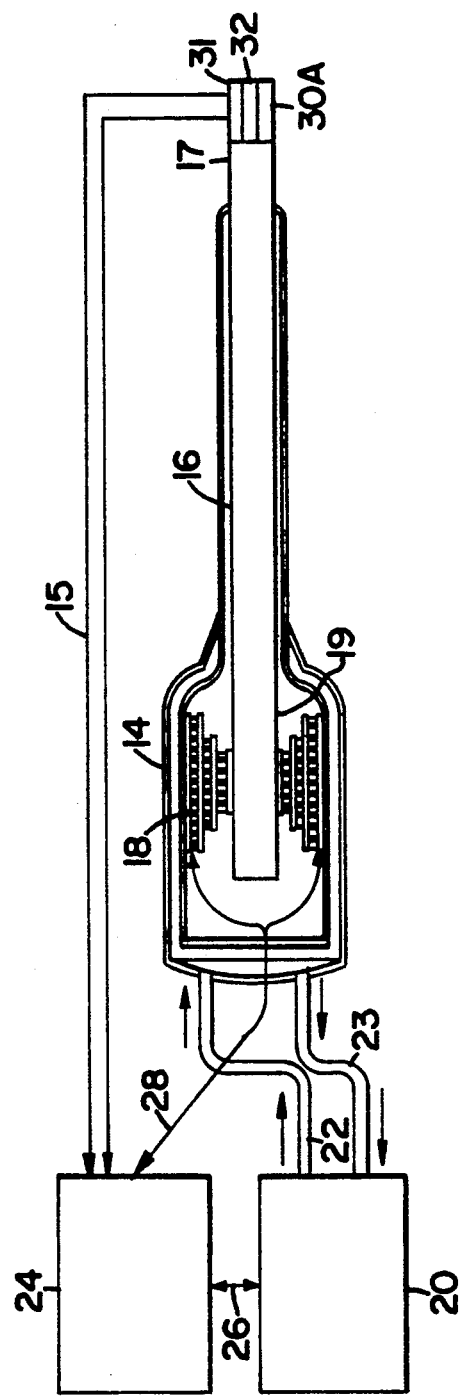

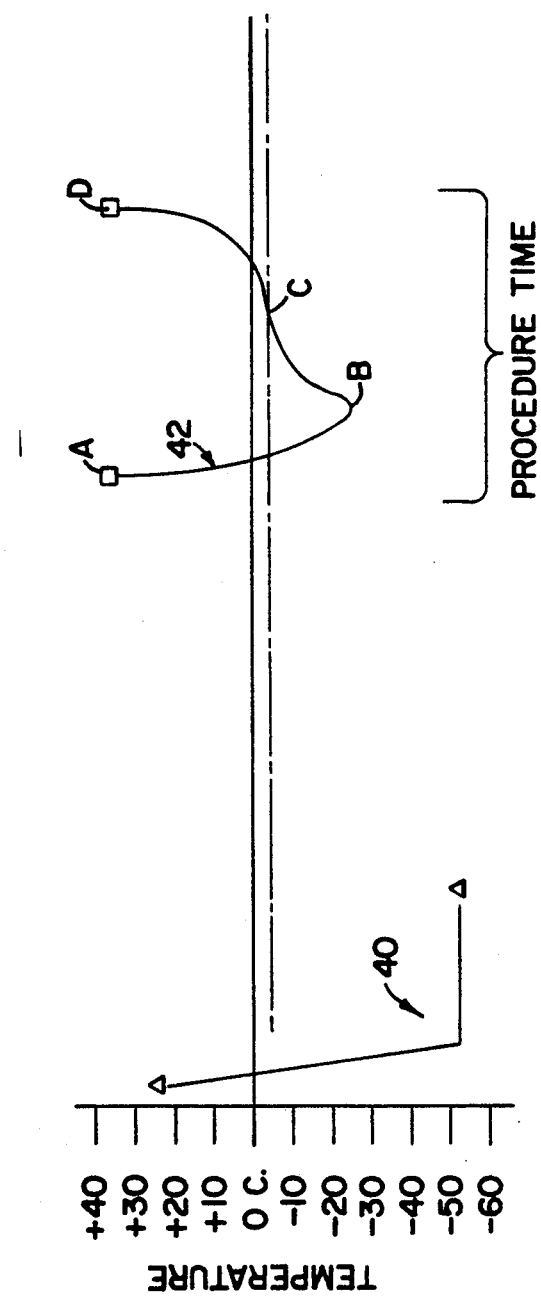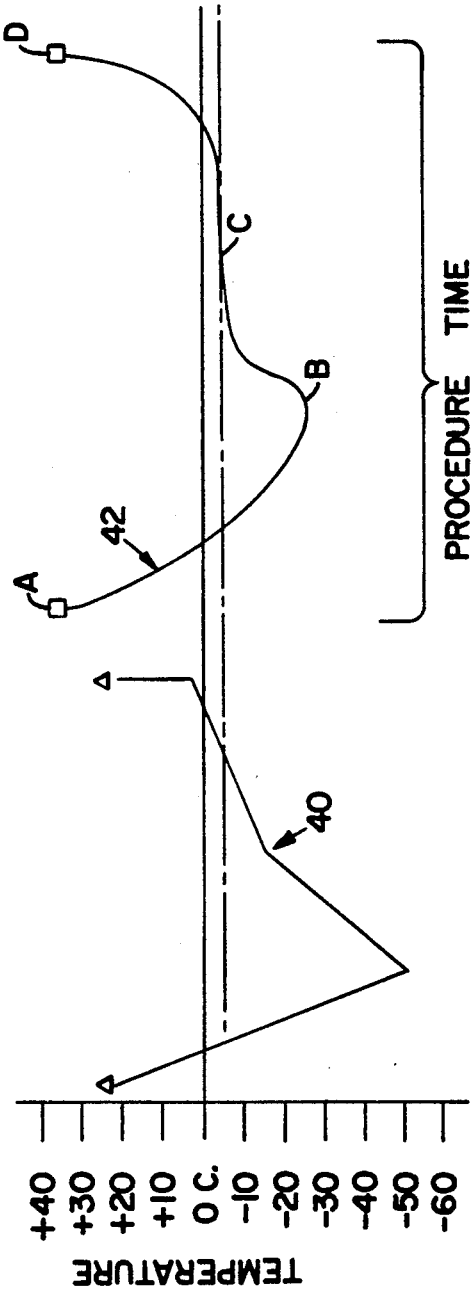

ELECTRONIC CRYOGENIC SURGICAL PROBE APPARATUS AND METHOD

BACKGROUND OF THE INVENTION

1. Field of the Invention

This invention relates generally to surgical instruments and more particularly to a thermoelectric cryosurgery tool and a method of using the same.

2. Description of the Prior Art

Cryosurgery, which relates to the destruction of living tissue by freezing cells, is commonly used to destroy benign and malignant tumors or neoplasms of the skin and mucous membranes. For example, cryosurgery is a commonly used treatment for warts, sun damage, keratoses, liver spots, and basal cell carcinoma.

Modified cryosurgery has also been used to treat inflammatory diseases of the skin, including acne. Cryotherapy has been used in nerve disorders such as the management of chronic pain and the heart disfunction AV-Node Reentrant tachycardia. Cryosurgery has also been effective in the ocular fields for open angle glaucoma treatment, cataract, and lens removal.

Cryosurgery is preferred to scalpel surgery for the treatment of many lesions because it is quick, rather painless, and often does not require local anesthesia, has a very low risk of infection post-operatively, and generally leaves a more cosmetically acceptable scar, if any. Cryosurgery is preferred to electrosurgery for the treatment of these lesions because the scar is cosmetically more acceptable and the depth of tissue destruction is greater.

The mechanisms, identified in the literature, causing cell destruction during cryosurgery, are several. First, if the cells are cooled slowly water leaves the cell resulting in high concentrations of toxic electrolytes which necritize. Second, if the rate of freeze is carried out too quickly, the ice crystals formed are small and less damage producing. During the thaw, if the "ice to water" phase change occurs too quickly, all ice simply melts. If thaw rates are slow, the ice crystals elongate as smaller crystals melt and refreeze to their neighbors, causing cell wall rupture. Lastly, cell death occurs when metabolism continues while ice blocks cell nutrient supply and waste disposal.

Cryosurgery may be performed through the direct application of refrigerants, such as dry ice, liquid nitrogen, nitrous oxide, or chlorofluorocarbons (CFC's) to the tissue at the treatment site. Methods of application include direct spray to the tissue, dipping a cotton swab into the liquid cryogen and then applying the soaked swab to the site or spraying the cryogen into a closed tip metal tube which is in contact with the site. However these techniques are undesirable for several reasons. First, the direct application of cryogens, dip or spray, causes a very fast freeze, resulting in the creation of tiny ice crystals instead of the large damage producing type. The cells also do not have time to dehydrate, reducing the damage caused by high electrolyte concentrations. After the cryogen is removed the heat from inside the body causes a relatively fast thaw, reducing the further elongation of ice crystals during the "ice to water" phase change, which occurs during a slower thaw rate. The application of spray into a closed tube gives some temperature rate control, but with great difficulty and imprecise cycle reproducibility. Second, some methods use CFC's which are hazardous to the environment, while others use nitrous oxide which can be toxic to the patient and physician. Thirdly, the literature states that many times the above treatments are not 100% effective due to the inability to induce enough of the mechanisms of destruction and the patient must return for successive treatments at later dates.

Fourth, the technique requires the purchase and storage of expensive, volatile refrigerants which quickly evaporate, no matter how well they are insulated. In addition, the direct use of refrigerants may expose the patient to the potential risk of cryoinjury resulting from refrigerant run-off or over-spray. Contamination of the refrigerant supply has also proved to be a drawback. Due to the expense, evaporation, and storage difficulties, general practitioners, small clinics, hospitals, military field hospitals, and underdeveloped countries do not normally keep cryogenic materials on hand, but refer their patients to a specialist, which causes greater inconvenience and cost to the patient.

It has been proposed to confine the refrigerant within a hollow cryoprobe. A cryoprobe typically includes a metal tip and a thermally insulated handle for holding a supply of the refrigerant. However, these probes also suffer from the storage and evaporation problems associated with the direct application of the refrigerants.

Beginning in approximately the 1960's, thermoelectric cryoprobes based on the Peltier effect of thermoelectric cooling were introduced. These probes utilized thermoelectric heat pumps, constructed from junctions of opposing P-type and N-type semiconductors. When an electric current is passed through the junction, the resulting electron flow pumps heat from the cold junction to the hot junction of the heat pump. A cascade of such devices, each cooling the hot junction of its neighbor, can reach cryogenic temperatures electrically, eliminating the need to store and apply dry or liquid refrigerants.

Examples of thermoelectric cryoprobes includes U.S. Pat. No. 3,502,080/Re26,276 (Hirschhorn), U.S. Pat. No. 3,369,549 (Armao) and U.S. Pat. No. 4,519,389 (Gudkin et al.).

Gudkin et al. discloses a semiconductor thermoelectric element mounted on a handle.

The Hirschhorn reference discloses a hand-held surgical instrument having a cutting edge or tool connected to a metal rod. The metal rod in turn is in direct physical contact with a plurality of Peltier elements, allowing the cutting edge or tool to be cooled considerably below ambient room temperature.

The Armao reference discloses a probe containing several thermoelectric elements capable of delivering either cryogenic or thermal temperatures for the treatment of tissue.

Typically, prior art devices have relied on solid metal thermal conductors and have operated the thermoelectric modules in parallel to increase the heat flow to the desired level. Configurations of this type are usually limited to a maximum temperature differential on the order of 65° C. The use of solid conductors also degrades performance because of the high temperature gradients supported by solid metallic conductors. A one-inch long copper or silver conductor is not suitable for cryosurgery, even if side losses are ignored, because of its high thermal resistance.

A heat pipe is a heat transfer device, usually tubular in shape, which is completely self contained, and has no moving mechanical parts. In general, cryogenic heat pipes are vacuum insulated. Cryogenic pipes have a condenser end which is cooled, causing the gas to condense. The condensed liquid is absorbed by a wick and flows by capillary action to the evaporator end. As heat is applied to the evaporator end, some of the liquid evaporates. This gas travels through the hollow center at near sonic speeds to the cooled, condenser end where it gives up heat, recondenses and starts the cycle again through the wick.

Heat pipes are useful since they assume a nearly isothermal condition while transporting large quantities of heat. Thus, heat pipes can transfer several hundred times the amount of heat that is transferred by metallic conductors at the same temperature drop. A properly designed heat pipe requires as little as one thousandth the temperature differential needed by a copper rod to transmit a given amount of power between two points.

In addition, heat pipes have the ability to regulate heat-flux transformation. As long as the total heat flow is in equilibrium, the fluid streams connecting the condenser and evaporator ends essentially are unaffected by the local heat flux in these regions. In fact, heat pipes which are two feet long lose only a couple of degrees from one end of the pipe to the other. A high heat flux input at one point of the evaporator end can be coupled with a large area of lower heat flux in the condenser end.

The direct application of liquid refrigerants is very effective because the physical evaporation of cryogens achieves a great flux density. The vaporization of cryogens in a heat pipe evaporator works the same without loss to the atmosphere.

Heat pipe models featuring flow through a closed end tube are nearly as effective as the above-described cryoprobe, with only a small thermal resistance at the end of the tube.

Cascades of Peltier devices are also known in the art. For example, *An Instrument Using a Multiple Layer Peltier Device to Change Skin Temperature Rapidly*, published in Brain Research Bulletin, Vol. 12, 1984, teaches a three layer Peltier device utilized in a pain research application. The device incorporates proportional feed back control to provide stable temperatures within the treated tissue.

None of the prior art Peltier instruments, including Frigitronics, are able to achieve temperatures lower than −25° to −35° C.

SUMMARY OF THE INVENTION

In contrast to this prior art, the present invention provides a handheld cryoprobe which includes a heat pipe structure coupled to a series cascade of several thermoelectric modules to provide a cryogenic heat sink. This cryogenic heat sink is connected to a treatment tip through the use of a heat pipe. Two configurations are contemplated.

In the first embodiment, the cascade of thermoelectric devices is coupled directly to the treatment tip via the heat pipe structure.

In the second embodiment, the cascade of thermoelectric devices is coupled to the treatment site through a heat pipe which carries an additional thermoelectric cooling module which may be bifurcated at its distal end. Although voltage polarity may be reversed to the tip module, creating a heating mode, this auxiliary thermoelectric element is referred to as a tip cooler throughout. When in a cooling mode, the tip module acts as an additional series fed refrigerating stage.

In either arrangement, each thermoelectric device in the cascade cools its neighbor, thus generating a steep temperature gradient. This cold source/heat sink is coupled to the heat pipe which connects to a replaceable distal probe tip.

The quick start up of the heat pipe permits the probe to improve the cooling rate in the tissue at the treatment site, which materially aids in the destruction of tissue, and significantly reduces the time required in surgery.

The structure of the present invention also includes a heat exchanger coupled to the cascaded thermoelectric cooling modules to reject heat from the application site into the air.

In operation, the distal end of the heat pipe is fitted with a disposable probe tip which is configured to meet the requirement of the specific surgical procedure. Alternatively, the tip itself may be configured as a heat pipe in order to avoid the thermal resistance of solid metal.

This device is capable of administering sustained cryogenic temperatures of approximately −60° to −70° C. to tissue proximate the distal probe tip, although temperatures of about −10° to −25° C. are sufficient in most cases. Probes and thermoelectric modules which are vacuum insulated are preferred when cryogenic temperatures below −60° C. are desired.

The thermoelectric coolers within the cryoprobe are regulated by a control system which may be programmed to cycle the power supplied to the thermoelectric modules to generate multiple freeze-thaw cycles with multiple controlled ramp rates within the tissue at the treatment site.

Although several treatment protocols may be practiced with the cryoprobe, the preferred treatment method involves multiple freeze-thaw cycles. In this application, the probe is operated to first form a frozen bolus of tissue at the treatment site. The tip cooler or primary cooler is then cycled to selectively thaw the center of the bolus and then refreeze the tissue periodically. This process leaves the exterior of the bolus frozen to protect outlying tissue.

In operation, the probe may be used to form a bolus of frozen tissue. The bolus may then be selectively thawed by reduction of cooling power supplied to the probe. In this mode of operation, the outer wall of the bolus remains substantially frozen and thus insulates the surrounding tissue from the cryogenic temperatures. This method of operation permits highly localized and selective destruction of tissue.

When a heat pipe without a tip thermoelectric module is utilized, the center of the tip may contain a resistance heater to effect thaw in the thaw procedure.

The selective destruction of tissue relies on several interrelated factors. For example, the outer wall of the frozen bolus prevents transport of nutrients and removal of metabolic waste products from the bolus, while the frozen barrier acts as a thermal insulator to localize and confine tissue destruction to the bolus volume. In addition, during the controlled rate thaw at the ice/water phase change, elongation of ice crystal growth is induced, causing mechanical damage to the cells.

BRIEF DESCRIPTION OF THE DRAWINGS

In the Drawings, like reference numerals indicate corresponding structure throughout the several views of the illustrative embodiment of the invention, in which:

FIG. 1 is a schematic diagram of the major elements of a first embodiment of the combination;

FIG. 2 is a schematic diagram of the major elements of a second embodiment of the combination including a tip cooler;

FIG. 3 is a schematic diagram of the major elements of a modified version of the second embodiment of the combination which includes a tip cooler having concentric cooling and heating zones;

FIG. 6 is a temperature-time history diagram illustrating a rapid phase change during the freeze/thaw cycle provided in accordance with state of the art procedures using liquid cryogens;

FIG. 6A is a temperature-time history diagram illustrating the extended phase change cycling provided in accordance with the principles of the present invention;

DETAILED DESCRIPTION OF THE PREFERRED EMBODIMENT

Figure 2A:
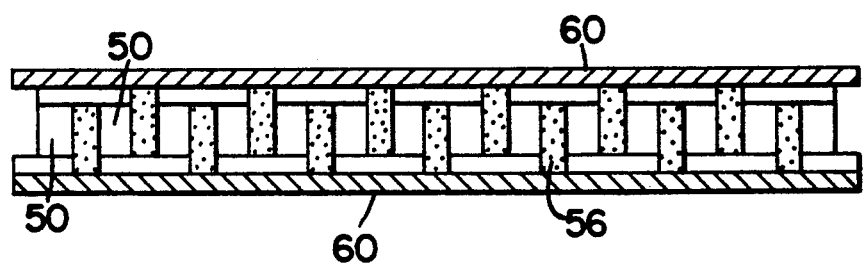
FIG. 2A is a cross-section view of a thermoelectric tip cooler module.

A schematic representation of the handheld electronic cryoprobe 10 is shown in FIG. 1. Cryoprobe 10 is used in conjunction with a disposable application or probe tip 12. Probe tip 12 can be of varying sizes, shapes and lengths, and has a biocompatible treatment surface in thermal contact with the distal end 17 of heat pipe 16. A handle 14 is provided to facilitate use of probe 10 by the physician. In general, cryoprobe 10 is reusable, since tip 12 is the only component which is disposable. In general, probe 10 may include a number of different handle and tip configurations to tailor the probe to a particular surgical procedure and/or the preference of a particular physician. For this reason, tip 12 and handle 14 are shown in schematic form.

The disposable probe tip 12 can contain thermoelectric and/or heat pipe materials, and is used as a trim cooler/heater to give fine temperature or control during the surgical procedure. A sterile sleeve (not shown) can be attached in the configuration so that it will slide over the heat pipe extension when installed. A quick snap-on connection (not shown) automatically makes power and thermocouple leads. Heat pipe extensions can also be quick-connected to the main power thermoelectrics in the handle (not shown), and contain power and thermocouple extension wiring for controlling the tip 12.

The proximal end 19 of heat pipe 16 is attached to Peltier effect thermoelectric cooling modules 18. Proximal cooling modules 18 draw heat from tip 12 and rejects it into a heat exchanger system depicted at 20. A liquid coolant such as tap or chilled water may be circulated through appropriate tubing 22, 23 to transfer heat from cryoprobe 10 to the remote heat exchanger 20 which in turn rejects the heat into the environment. Tubing 22, 23 may be made, for instance, of any well known plastic material, and may be insulated.

Alternatively, to get the heat from the thermoelectrics in handle 14 to the remote heat exchanger 20, it is possible to use a circulating liquid system where supply and return liquid channels and wiring are contained within one tube (not shown). This tube will have a closed cell insulation extruded over the channels, with an outer protective sheath, such as silicone.

Heat pipe 16 is of a typical heat pipe construction known in the industry, as described above, having a closed thin wall tube with its inner wall covered with a capillary wick composed of several layers of fine material such as mesh screen, sintered metal wool, or powdered metal. Preferably, heat pipe 16 and thermoelectric modules 18 are vacuum insulated. Heat pipe 16 is evacuated and a volatile fluid, such as ammonia, is metered into the tube to a proper vapor pressure. Cryogenic heat pipe 16 has a condenser end 19 and an evaporator end 17. The condenser end 19 is cooled, and the gas condenses. The condensed liquid is absorbed by the wick and flows via capillary action to the evaporator end 17. As heat is applied to the evaporator end 17, some of the liquid evaporates to a gaseous state. High efficiency is achieved through the phase change of the liquid to its gaseous state. This gas travels at near sonic speeds through the hollow center to the cooled condenser end 19 where it gives up its heat. The gas recondenses and starts the cycle again through the wick. Thus, the heat pipe is a closed cycle refrigerator which has no moving mechanical parts, and is powered externally by the thermoelectric materials.

Thermoelectric cooling modules 18 are essentially a multi-stage thermoelectric heat pump assembly containing numerous cascaded N-type semiconductors and P-type semiconductors well known in the art. Electrons in the N-type semiconductors and holes in the P-type semiconductors move heat from the cool body to a heat sink where the heat is removed.

A control unit 24 is provided to manage the power requirements of the system. Control unit 24 supplies power through a connection 26 to control the circulation of coolant in heat exchanger 20. Control unit 24 also provides electrical power to the proximal thermoelectric modules 18 through a connection 28. Control unit 24 may be programmed to cycle the power to the thermoelectric modules 18. Connection 26 and connection 28 can be any connection commonly used in the industry.

In general, the amount of D.C. voltage supplied to thermoelectric modules 18 controls the heat transfer rate of the module because heat moves through the N and P-doped semiconductor relative to the current flow, which in turn varies with voltage application. In operation, feedback sensors may be located at the tissue treatment site to provide temperature information to control unit 24 which is used to cycle power to the thermoelectric modules 18.

In the FIG. 1 embodiment, temperature feedback is provided from the treatment site by a remote sensor 13 which is integrated into disposable treatment tip 12. In general, one sensor 13 is sufficient on tip 12, although more may be utilized. Remote hypodermic thermocouple probes located in the tissue being frozen may also be used to provide the temperature feedback information. As shown in FIG. 1, temperature data from the treatment site is supplied to the control module 24 through a connection 15. Connection 15 can be any connection commonly used in the industry.

With respect to the FIG. 1 embodiment, the temperature cycling of the tissue is accomplished by power regulation of proximal cooler 18, and is mediated by heat pipe 16 and the passive treatment tip 12.

It should also be understood that a thermoelectric device itself can be operated as a temperature sensor. In embodiments where a distal Peltier effect thermoelectric tip cooler module 30, 30a is located proximate the treatment site, the thermoelectric tip module 30, 30a can be operated to provide temperature feedback information by their respective current flows, since current flow in thermoelectric materials is directly related to their temperature. This configuration is shown in the embodiment depicted in FIG. 2 and FIG. 3.

FIG. 2A sets forth a cross-section view of thermoelectric tip cooler module 30. Tip module 30 is made of P and N semiconductor couples 50 positioned between voids 56 which are filled with a thermally conductive material, such as thermally conductive epoxy. Insulating ceramic 60, such as aluminum oxide, sandwiches the P and N couples 50 and the voids 56 filled with conductive material.

With respect to the FIG. 2 or FIG. 3 embodiment, the battery of proximal thermoelectric modules 18 provides powerful cooling, reducing the temperature of the treatment site to that needed for the surgical procedure. At this point, a distal or thermoelectric tip cooler 30, 30a, powered by control unit 24, may selectively cool or heat the treatment site to provoke a designed or specified freeze/thaw cycle, thus promoting damage to the tissue by controlling the rate of water/ice or ice/water phase change. The distal or tip thermoelectric 30, 30a, which can work as a cooler or heater by switching the voltage polarity from the DC power supply, serves to fine tune the temperature at the treatment site into a very accurate range, or a designed freeze/thaw cycle. In addition, distal or thermoelectric tip 30, 30a is utilized to control the freeze/thaw rate.

Figure 5:
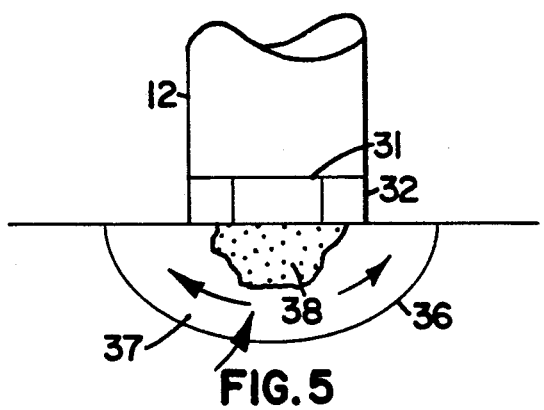
FIG. 5 is an illustration of the ice bolus formed by cycled application of the cryoprobe having a bifurcated thermoelectric tip assembly.

The apparatus shown in FIG. 3 includes a bifurcated thermoelectric tip module 30a having two concentric zones. Each zone is separately operated so it can be heated or cooled. When bifurcated thermoelectric module 30a has both zones in a cooling mode, an ice ball 36 will form, as shown in FIG. 5. Each of the zones may be operated separately so that the co-central zone 31 may be operated as a heater while the adjacent annulus 32 may be operated as a cooler, or vice versa, to freeze or thaw the tissue within ice bolus 36.

In FIG. 2 and FIG. 3, proximal cascade thermoelectric module 18 is coupled to the treatment site through a heat pipe which connects to disposable thermoelectric tip module 30, 30a at the distal end 17 of heat pipe 16. Feedback information in FIG. 2 and FIG. 3 is supplied to control unit 24 by connection 15, as discussed above.

Figure 4:
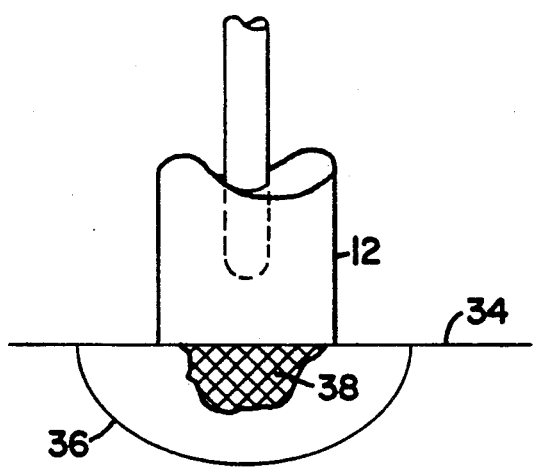
FIG. 4 is an illustration of the ice bolus formed by application of a conventional cryoprobe using compressed gas sprayed on the inside of the tip.
Figure 4A:
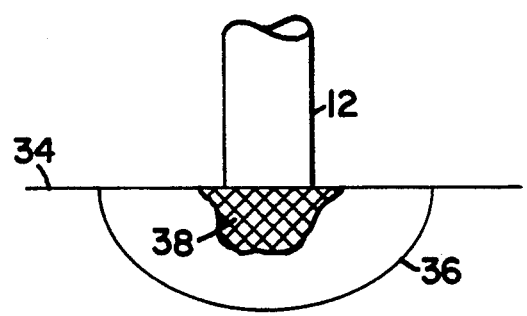
FIG. 4A is an illustration of the ice bolus formed by application of a heat pipe cryoprobe cooled thermoelectrically.
Figure 5A:
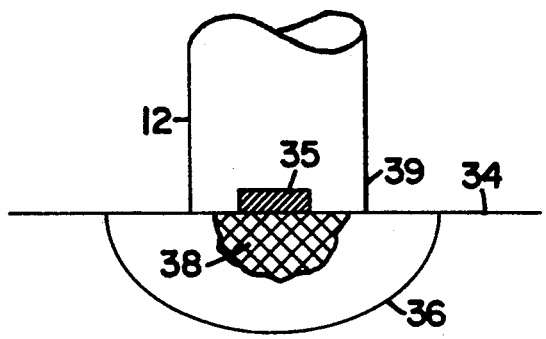
FIG. 5A is an illustration of the ice bolus formed by cycled application of a heat pipe having a resistance heater.
Figure 7:
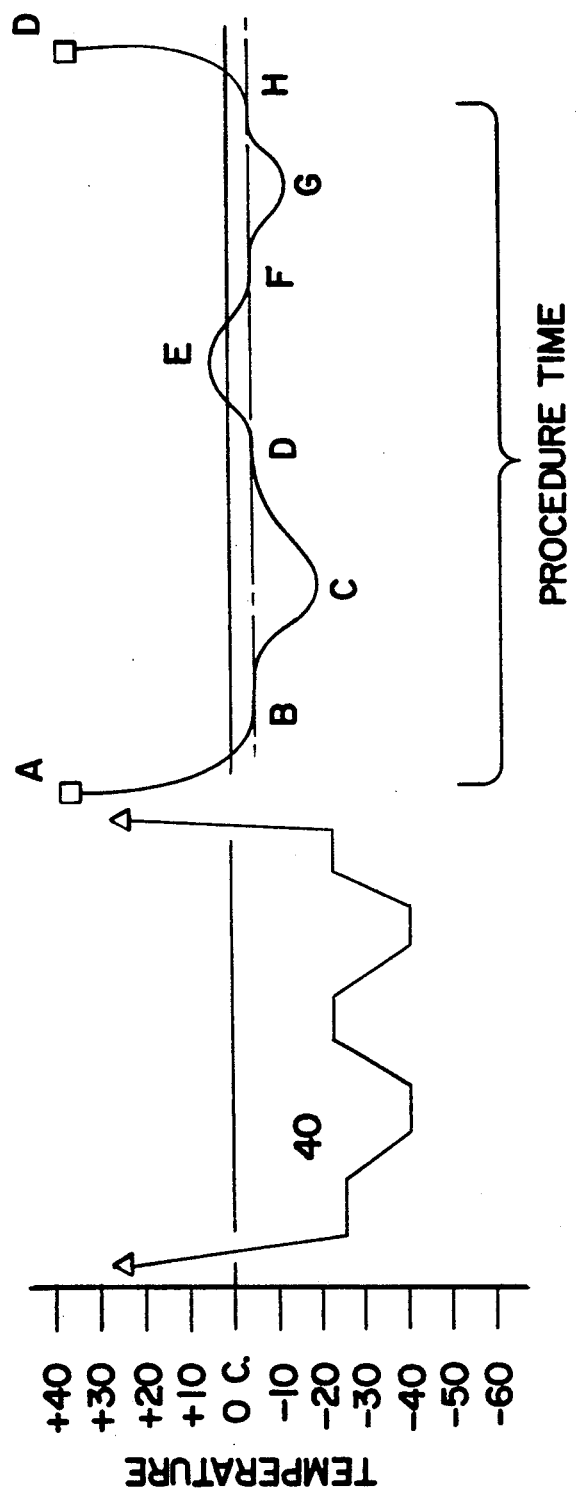
FIG. 7 is a temperature-time history diagram illustrating the multiple freeze thaw cycling provided in accordance with the principles of the invention.

The preferred treatment modality using the FIG. 1 or 2 apparatus is depicted in FIG. 4A. The preferred treatment modality using the FIG. 3 apparatus is depicted in FIG. 5. The preferred treatment modality using a heat pipe tip with a resistance heater is shown in FIG. 5A. The temperature-time history diagrams of FIGS. 6, 6A and 7 are applicable to, and may be generated by any of the above treatment modalities.

FIG. 4 illustrates the existing procedure where a treatment probe tip 12 is in contact with tissue 34 surface at a treatment site. Compressed cryogen gas is sprayed on the inside of hollow probe tip 12. As probe tip 12 is placed in contact with the tissue 34 surface, the expanding cryogen gas cools probe tip 12 to the desired operating temperature, such that an ice ball 36 is formed at and below the surface of tissue 34. Ideally, probe tip 12 is positioned so that the ice ball or bolus 36 which forms includes or encompasses the target, abnormal tissue or lesion 38 and a small amount of normal tissue 34. After the cryoprobe 10 is removed, ice ball 36 begins to quickly thaw from the inside to the exterior.

FIG. 4A illustrates heat pipe 16 with tip 12 in contact with the tissue 34 surface. As electricity is supplied to the proximal cooler 18, heat pipe 16 is lowered to operating temperatures of about $-70°$ C. Tip 12 on heat pipe 16 is positioned on the surface of tissue 34. As the tissue temperature decreases, ice ball or bolus 36 forms, so as to surround and encompass the target, abnormal tissue 38 and a small amount of normal tissue 34. After heat pipe 16 power is reduced, ice ball 36 begins to slowly thaw from the interior to the exterior.

Probe 10 is operated to selectively thaw that portion of ice bolus 36 which is adjacent probe tip 12. Selective thawing of bolus 36 is achieved by reduction of cooling power supplied to probe 10. The power level supplied to probe 10 can be varied to prevent ice bolus 36 from completely thawing. Temperature feedback can be used to control the delivery of power to the probe 10 to provide the alternating freeze and thaw cycles, or the power level can be preprogrammed to follow a preset power delivery protocol.

FIG. 5 illustrates an ice ball 36 formed when the bifurcated thermoelectric tip cooler module 30a shown in FIG. 3 has both zones in the cooling mode. After the initial ice ball or bolus 36 is formed, the co-central zone 31 can be switched to a heating mode while keeping the adjacent annulus zone 32 in a cooling mode. By this technique, the target abnormal tissue or lesion 38 can be brought to a metabolizing temperature while the outer wall of bolus 36 remains substantially frozen. Target tissue 38, as it is warmed, comprises water and water metabolizing stored nutrients. Ice in ice ball 36 is approximately four times as heat conductive as the liquid water in tissue 38. Thus, the outer cooled zone 37 surrounding target tissue 38 maintains the nutrient blocking ice shield.

Alternatively, as shown in FIG. 5A, a heat pipe 16 tip 12 can include a thin film heater 35 (made from an etched-foil resistive element laminated between layers of insulating film of the tip 12 such as Thermofoil TM manufactured by Minco Products, Inc.). Thin film heater 35 performs the same function as inner thermoelectric zone 31 shown in FIG. 5. Heat pipe conduction 39 performs the same function as outer thermoelectric zone 32 in FIG. 5. Thus, thin film heater 35 can be used in a heating mode while heat pipe conduction 39 remains in a cooling mode so that target, abnormal tissue 38 can be brought to a metabolizing temperature, while the outer wall of bolus 36 remains substantially frozen, insulating the surrounding tissue from nutrient supply.

The apparatus of the present invention may also be used to provoke multiple freeze-thaw phase changes in the treated tissue which are generated by selectively regulating the voltage delivered to the thermoelectric cooling modules. Such regulation can be accomplished by selectively increasing and decreasing the voltage delivered to the thermoelectric cooling modules 30, 30a to cool the treated tissue, followed by reversing the polarity of the voltage delivered to the thermoelectric cooling modules 30, 30a to warm the treated tissue. It should be further understood that the freeze-thaw phase changes can be generated by regulating the voltage delivered to either one or both of the thermoelectric cooling modules 18, 30, 30a. In addition, the precise regulation of the phase changes may be accomplished through the use of a control and temperature sensor feedback system, where an embedded hypodermic thermocouple transmits temperature information to a microprocessor which monitors the rate of temperature change relative to time, thus detecting the phase change. The microprocessor then applies power to the thermoelectric modules so as to extend the phase change time, thereby causing maximum ice crystal growth. This type of control is known commonly in industrial process control as PID (proportional, integral, derivative) control. Finally, when both thermoelectric modules 30/30a and proximal thermoelectric cooling modules 18 are utilized, freeze-thaw cycling may be accomplished by holding the thermoelectric cooling modules 30/30a at a constant, near-freezing temperature, while regulating the voltage delivered to the proximal cooling module 18. Multiple controlled ramp rates may be replaced in the above manner thus insuring complete tissue destruction in a single treatment.

The time/temperature histories more fully describe this operation. In FIG. 6, the temperature profile 40 shows the temperature history of the surface being contacted by a liquid cryogen while profile 42 shows the temperature profile a short distance inside the tissue treatment site. At point A in profile 42, the tissue is at ambient temperature. The direct application of a liquid cryogen or hollow closed end tube being cooled by direct spray of a cryogen produces a steep drop in temperature in the tissue until it is removed as indicated at low point B. The tissue undergoes a natural thaw returning the temperature to ambient at point D. The inflection of the temperature time history at C, reflects the relatively rapid phase change from the solid to liquid phase. Some ice crystal elongation does develop during the thaw, normally not enough to assure effectiveness, for this reason normal procedures call for a second application after the thaw when treating cancer lesions. Additionally the freeze rate is so rapid that no phase change inflection can be detected during the temperature drop, thereby resulting in less damaging, very small ice crystals. These procedures depend on ice crystal growth solely during thaw to produce damage. In contrast to the direct application of liquid cryogens, FIG. 6A shows the time vs. temperature histories of the thermoelectrically powered probe. The temperature profile 40 shows the temperature history of the probe tip while 42 once again shows that temperature a short distance inside the tissue treatment site. At point A in profile 42, the tissue is at ambient temperature. The application of power to the thermoelectric modules 18 results in cooling the tissue below the freezing point, to a low temperature designated as B, in FIG. 6. The temperature drop is created by multi-stage thermoelectrics in the handle of the probe 10, and heat is extracted from the condenser end of the heat pipe. The evaporator end of heat pipe 16 is placed against target tissue 38 where it removes body heat at a rate shown by profile 42. At this point, the electrical power to the thermoelectric modules 18 is turned off or reduced, and tissue 38 undergoes a warming cycle, returning the temperature of the tissue to ambient at D. In general, this temperature vs. time history emulates the application of a prior art liquid refrigerant directly on the tissue as shown in FIG. 6. However, in contrast to the prior art, the rate at which the tissue is frozen is a feedback controlled function with an extended phase change induced during the freeze portion of the cycle. In a similar fashion the B to D transition can be controlled as well, and the phase change time during the thaw cycle can be extended. Control over the solid to liquid phase transition can be used to maximize the amount of tissue damage resulting from the ice crystal growth and elongation invoked by the controlled slow thaw cycle.

Direct application of the thermoelectric modules can achieve temperatures in the range of −25° C. However, the addition of heat pipe 16 improves the ability of the surgeon to manipulate the cryoprobe device 10 and allows the use of the larger thermoelectric modules needed for the colder temperatures and proper depth of freeze. In addition, use of the heat pipe 16 provides a means to reach into cavities. Heat pipe 16 can also be made flexible by using many thin walled microbore tubes in its construction to provide the gas and liquid transport areas of the pipe between the condenser and evaporator tip.

FIG. 7 is a graphical illustration of the preferred multiple freeze-thaw phase changes that occur in treated tissue over time as a result of cycled application of cryogenic temperatures when a thermoelectric application tip 30 is added to the electronic cryoprobe 10 of the present invention. In operation, the initial temperature of the tissue at A is at or above room temperature. The multistage thermoelectric module 18, attached to the heat pipe 16 condenser end, drops the temperature initially to a less cold level B.

Thermoelectric tip 30, or 30a added to the cold end of heat pipe 16 is applied to the site being treated, and heat is extracted or added as required to accomplish the tissue freeze/thaw procedure, shown at B, C, D, E, F, G, H and I in FIG. 7. Very accurate and quick temperature changes can be pre-programmed using an embedded microprocessor to accomplish a positive procedure. With the coldest temperatures being generated at tip 30 or 30a, probe 10 may be inserted into more restricted and deeper cavities without the chance of damaging normal wall tissue.

As can be appreciated, use of cryoprobe 10 using a bifurcated thermoelectric tip cooler module 30a creates an ice shield which prevents the flow of nutrients resulting from the thaw of tissue 38, thereby ensuring cell starvation. A hand-held cryoprobe 10 eliminates the need for compressed gases, while giving the physician positive control. In addition, because solid state electronics lends itself to miniaturization, cryosurgical devices will have many uses, including possible use with endoscopes.

While the invention has been described in detail with particular reference to the drawings and illustrative embodiment, it should be understood that modifications will be effected within the spirit and scope of the invention.

I claim:

1. An electronic cryoprobe for treating tissue comprising:

a) a thermoelectric cooling module;

b) a heat pipe coupled to said thermoelectric cooling module wherein heat is transferred from said heat pipe to said cooling module;
c) an application tip coupled to said heat pipe wherein heat is transferred from a tissue treatment site to said heat pipe;
d) an electric power means for supplying power to said thermoelectric cooling module;
e) a control means connected to said thermoelectric cooling module for regulating the rate of heat transferred by said cooling module; and
f) a sensing means connected to said control means for detecting the heat loss transferred from said treatment site to said electronic cryoprobe, wherein said sensing means relays temperature information to said control means, and wherein said control means processes said information to generate a multiple freeze-thaw cycle to be delivered by said electronic cryoprobe to said treatment site.

2. The electronic cryoprobe of claim 1 further comprising a heat exchanging means coupled to said cooling module for transferring heat from said cooling module to said heat exchanging means.

3. The electronic cryoprobe of claim 1 wherein said multiple freeze-thaw cycle is generated by the control means selectively increasing, and then selectively decreasing the voltage from said electric power means to said thermoelectric cooling module and wherein said selective increasing and decreasing in voltage is continued until the tissue being treated is destroyed.

4. The electronic cryoprobe of claim 1 wherein said multiple freeze-thaw cycle is generated by the control means selectively delivering constant voltage from said electric power means to said thermoelectric cooling module, causing the tissue to be cooled, followed by the said control means reversing the polarity of the voltage delivered to said thermoelectric module, causing the tissue to be warmed, and wherein said cycling in voltage polarity is continued until the tissue being treated is destroyed.

5. The electronic cryoprobe of claim 1 wherein said sensing means is coupled to the application tip of said cryoprobe.

6. The electronic cryoprobe of claim 1 wherein said sensing means is placed within the tissue subject to treatment.

7. The electronic cryoprobe of claim 6 wherein said sensing means consists of hypodermic thermocouple capable of being imbedded in said tissue.

8. The electronic cryoprobe of claim 1 wherein said heat pipe is capable of being detachably coupled to said thermoelectric cooling module.

9. The electronic cryoprobe of claim 1 wherein said application tip is capable of being detachably fitted to said heat pipe.

10. The electronic cryoprobe of claim 2 wherein said thermoelectric cooling module is capable of generating sustained temperatures of at least $-55°$ C. by transferring heat from said cooling module to said heat exchanging means.

11. An electronic cryoprobe for treating tissue comprising:
a) a thermoelectric cooling module wherein upon being provided with electric power said cooling module displays opposing hot and cold surfaces;
b) a heat pipe coupled to said thermoelectric cooling module wherein heat is transferred from said heat pipe to the cold surface of said cooling module;
c) an application tip coupled to said heat pipe wherein heat is transferred from a tissue treatment site to said heat pipe;
d) a heat exchanging means coupled to the hot surface of said cooling module for transferring heat from said cooling module to said heat exchanging means and into the ambient air;
e) a control means connected to said thermoelectric cooling module for regulating the rate of heat transferred by said cooling module; and
f) a sensing means connected to said control means for detecting the heat loss transferred from said treatment site to said electronic cryoprobe, wherein said sensing means relays temperature information to said control means, and wherein said control means processes said information to generate a multiple freeze-thaw cycle to be delivered by said electronic cryoprobe to said treatment site.

12. The electronic cryoprobe of claim 11 wherein said multiple freeze-thaw cycle is generated by the control means selectively increasing, and then selectively decreasing the voltage from said electric power means to said thermoelectric cooling module and wherein said selective increasing and decreasing in voltage is continued until the tissue being treated is destroyed.

13. The electronic cryoprobe of claim 11 wherein said multiple freeze-thaw cycle is generated by the control means selectively delivering constant voltage from said electric power means to said thermoelectric cooling module, causing the tissue to be cooled, followed by the said control means reversing the polarity of the voltage delivered to said thermoelectric module, causing the tissue to be warmed, and wherein said cycling in voltage polarity is continued until the tissue being treated is destroyed.

14. The electronic cryoprobe of claim 11 wherein said sensing means is coupled to the application tip of said cryoprobe.

15. The electronic cryoprobe of claim 11 wherein said sensing means is placed within the tissue subject to treatment.

16. The electronic cryoprobe of claim 15 wherein said sensing means consists of hypodermic thermocouple capable of being imbedded in said tissue.

17. The electronic cryoprobe of claim 11 wherein said heat pipe is capable of being detachably coupled to said thermoelectric cooling module.

18. The electronic cryoprobe of claim 11 wherein said application tip is capable of being detachably fitted to said heat pipe.

19. The electronic cryoprobe of claim 11 wherein said thermoelectric cooling module is capable of generating sustained temperatures of at least $-55°$ C. by transferring heat from said cooling module to said heat exchanging means.

20. An electronic cryoprobe for treating tissue comprising:
a) a first thermoelectric cooling module;
b) a heat pipe coupled to said first thermoelectric cooling module wherein heat is transferred from said heat pipe to said first cooling module;
c) an application tip coupled to said heat pipe wherein heat is transferred from said tissue site to said heat pipe; and d) a second thermoelectric cooling module coupled to said application tip wherein heat is transferred from said tip to said heat pipe.

21. The electronic cryoprobe of claim 20 further comprising a control means connected to said first thermoelectric cooling module for regulating the rate of heat transferred by said cooling module.

22. The electronic cryoprobe of claim 21 further comprising a sensing means connected to said control means for detecting the heat loss transferred from said treatment site to said electronic cryoprobe, wherein said sensing means relays temperature information to said control means, and wherein said control means processes said information to generate a multiple freeze-thaw cycle to be delivered by said electronic cryoprobe to said treatment site.

23. The electronic cryoprobe of claim 22 wherein said multiple freeze-thaw cycle is generated by the said control means selectively increasing, and then selectively decreasing the voltage from said electric power means to said thermoelectric cooling module and wherein said selective increasing and decreasing in voltage is continued until the tissue being treated is destroyed.

24. The electronic cryoprobe of claim 22 wherein said multiple freeze-thaw cycle is generated by the said control means electively delivering constant voltage from said electric power means to said thermoelectric cooling module, causing the tissue to be cooled, followed by the said control means reversing the polarity of the voltage delivered to said thermoelectric module, causing the tissue to be warmed, and wherein said cycling in voltage polarity is continued until the tissue being treated is destroyed.

25. The electronic cryoprobe of claim 22 wherein said sensing means is coupled to the application tip of said cryoprobe.

26. The electronic cryoprobe of claim 22 wherein said sensing means is placed within the tissue subject to treatment.

27. The electronic cryoprobe of claim 26 wherein said sensing means consists of hypodermic thermocouple capable of being imbedded in said tissue.

28. The electronic cryoprobe of claim 20 wherein said heat pipe is capable of being detachably coupled to said thermoelectric cooling module.

29. The electronic cryoprobe of claim 20 wherein said application tip is capable of being detachably fitted to said heat pipe.

30. The electronic cryoprobe of claim 20 wherein said thermoelectric cooling module is capable of generating sustained temperatures of at least $-55°$ C. by transferring heat from said cooling module to said heat exchanging means.

31. A method of destroying and thereby treating benign and malignant tumors of the skin and mucous membranes comprising the steps of:
a) transferring heat from a tissue treatment site to form a frozen bolus;
b) monitoring said heat loss; and
c) administering a freeze-thaw cycle to said tissue treatment site while maintaining a frozen outer wall of said bolus.

* * * * *